US009469438B2

(12) United States Patent
Nool

(10) Patent No.: US 9,469,438 B2
(45) Date of Patent: Oct. 18, 2016

(54) PIM HOLDER WITH CLAMPING DEVICE

(71) Applicant: Volcano Corporation, San Diego, CA (US)

(72) Inventor: Jeffrey A. Nool, Elk Grove, CA (US)

(73) Assignee: Volcano Corporation, San Diego, CA (US)

( * ) Notice: Subject to any disclaimer, the term of this patent is extended or adjusted under 35 U.S.C. 154(b) by 369 days.

(21) Appl. No.: 13/933,835

(22) Filed: Jul. 2, 2013

(65) Prior Publication Data

US 2014/0007408 A1    Jan. 9, 2014

Related U.S. Application Data

(60) Provisional application No. 61/667,742, filed on Jul. 3, 2012.

(51) Int. Cl.
*A47B 96/06* (2006.01)
*B65D 25/22* (2006.01)
(Continued)

(52) U.S. Cl.
CPC .............. *B65D 25/22* (2013.01); *A61G 13/101* (2013.01); *A61M 5/1418* (2013.01); *Y10T 29/49947* (2015.01)

(58) Field of Classification Search
CPC .............. A61G 13/101; A61M 5/1418; Y10T 29/49947; A61B 19/26; A61B 2019/267; A61B 2019/268; F16B 2/10; F16B 2/18; F16B 2/185
USPC ......................................................... 248/214
See application file for complete search history.

(56) References Cited

U.S. PATENT DOCUMENTS 4,832,299 A  *  5/1989  Gorton ..................... A61G 7/05
                                                    248/231.71
4,852,841 A  *  8/1989  Sebring ................ A61G 13/101
                                                    24/514

(Continued)

FOREIGN PATENT DOCUMENTS

DE             3149215 A1      6/1983
WO        WO 95/10389 A1      4/1995

OTHER PUBLICATIONS

International Searching Authority/KIPO, "Notification of Transmittal of the International Search Report and The Written Opinion of the International Searching Authority, or the Declaration," for PCT/US2013/048626, mailed Sep. 4, 2013, 12 pages.

(Continued)

*Primary Examiner* — Christopher E Garft
(74) *Attorney, Agent, or Firm* — Haynes and Boone, LLP

(57) ABSTRACT

A PIM holder for attaching a PIM device having a cable to a rail in a medical environment includes a holster and a clamping device. The holster includes an open end sized to receive a PIM device and includes a cable opening extending from the open end on a side adjacent the open end to a side opposite the open end. The clamping device is sized and configured to attach the holster to a rail. The clamping device includes a stationary jaw secured to the holster and a moving jaw disposed adjacent the stationary jaw. The stationary jaw and moving jaw form an opening that receives the rail in a lateral direction and forms a passage therebetween to capture the rail. An actuator is pivotable between an open position and a closed position to displace the moving jaw to open and close the clamping device.

11 Claims, 18 Drawing Sheets

(51) Int. Cl.
*A61M 5/14* (2006.01)
*A61G 13/10* (2006.01)

(56) References Cited

U.S. PATENT DOCUMENTS

| | | | | | |
|---|---|---|---|---|---|
| 4,854,016 | A | * | 8/1989 | Rice | A61G 13/101 24/494 |
| 4,998,277 | A | * | 3/1991 | Rioux, Jr. | H04M 1/04 248/214 |
| 5,176,343 | A | * | 1/1993 | Cheney, II | H01R 13/60 248/214 |
| 5,320,314 | A | * | 6/1994 | Bookwalter | A61B 17/02 24/525 |
| 5,829,723 | A | * | 11/1998 | Brunner | A61M 5/1413 248/222.13 |
| 5,938,160 | A | * | 8/1999 | Hartmann | B60N 3/103 224/926 |
| 6,085,952 | A | * | 7/2000 | Garland | A45F 5/021 224/242 |
| 6,598,275 | B1 | * | 7/2003 | Kolody | A61G 13/101 24/455 |
| 7,398,951 | B1 | * | 7/2008 | Sugalski | A61G 7/0503 248/214 |
| 7,556,616 | B2 | | 7/2009 | Fathallah | A61M 5/1413 604/131 |
| 7,669,816 | B2 | * | 3/2010 | Crain | F16M 13/02 248/183.3 |
| 7,712,713 | B2 | * | 5/2010 | Kankkunen | F16M 13/022 248/214 |
| 7,770,855 | B2 | * | 8/2010 | Locke | A61M 5/1415 248/214 |
| 7,866,617 | B2 | * | 1/2011 | Kleitsch | A61M 5/1417 248/228.5 |
| 8,490,937 | B2 | * | 7/2013 | Crain | F16M 13/02 224/929 |
| 9,022,334 | B1 | * | 5/2015 | DeMayo | A61G 13/101 248/229.22 |
| 2003/0106917 | A1 | * | 6/2003 | Shetler | A45F 5/02 224/197 |
| 2003/0155478 | A1 | * | 8/2003 | Easterling | A61G 15/10 248/316.1 |
| 2003/0236463 | A1 | | 12/2003 | Mesaros et al. | |
| 2005/0004470 | A1 | | 1/2005 | Camus et al. | |
| 2006/0192064 | A1 | * | 8/2006 | White | A61C 19/00 248/213.2 |
| 2007/0232933 | A1 | * | 10/2007 | Gille | A61B 5/02007 600/481 |
| 2008/0203644 | A1 | | 8/2008 | DaSilva | |
| 2009/0013507 | A1 | * | 1/2009 | Scott | A61G 13/101 24/502 |
| 2009/0236254 | A1 | * | 9/2009 | Jenkins | B65D 25/22 206/459.5 |
| 2010/0299890 | A1 | * | 12/2010 | Doyle | A61G 7/05 24/457 |
| 2011/0101587 | A1 | * | 5/2011 | Quintania | B25B 5/006 269/74 |
| 2012/0126079 | A1 | * | 5/2012 | Russell | A61G 13/101 248/229.23 |
| 2012/0241571 | A1 | * | 9/2012 | Masionis | A61G 1/04 248/214 |
| 2013/0019883 | A1 | * | 1/2013 | Worm | A61G 13/101 128/882 |
| 2013/0277932 | A1 | * | 10/2013 | De Jong | B62B 3/10 280/79.11 |
| 2014/0007408 | A1 | * | 1/2014 | Nool | B65D 25/22 29/525.01 |
| 2014/0203550 | A1 | * | 7/2014 | Utsch | F16L 37/1205 285/308 |
| 2014/0205371 | A1 | * | 7/2014 | Bally | A61G 12/008 403/327 |
| 2015/0094780 | A1 | * | 4/2015 | Krickeberg | A61G 13/101 606/86 R |
| 2015/0306305 | A1 | * | 10/2015 | Kluttz | A61M 5/1418 248/219.4 |
| 2015/0320930 | A1 | * | 11/2015 | James | F16L 3/23 5/503.1 |

OTHER PUBLICATIONS

European Patent Office, "Communication pursuant to Rule 164(1)" EPC, partial supplementary European search report for EP 131813765.8 mailed Jan. 18, 2016, 7 pages.

* cited by examiner

PIM HOLDER WITH CLAMPING DEVICE

CROSS REFERENCE TO RELATED APPLICATIONS

The present application claims priority to and the benefit of U.S. Provisional Patent Application No. 61/667,742, filed Jul. 3, 2012, which is hereby incorporated by reference herein in its entirety.

BACKGROUND

This invention relates generally to holders for patient interface modules (PIM) and more particularly, to PIM holders with clamping systems for connecting to rails.

Surgical tables frequently have side rails attached thereto that support attachments and accessories commonly required during medical procedures. The side rails typically extend along opposing sides of the surgical table. For example, some surgical procedures require the use of PIM that may be hung on the rail adjacent the patient.

Attachment of the PIM to the rails is conventionally accomplished using rigidly, fixed clamps that use knob screws that require many turns to tighten the clamps onto the rail in a fixed and rigid position. Other attachment systems are hooks that hang from the rails. These have a tendency to permit the PIM to swing as the bed moves, bumping into nearby elements and creating distracting noise. Others are fixed in place on the rail, requiring special tools to disconnect the clamps so they can be reoriented in a separate position, and then to reattached using the same special tool. They are typically unable to be solid enough to support the accessories and still be easily adjusted, moved, or reoriented in convenient positions.

What is needed is a PIM holder that can be efficiently, yet securely clamped onto a rail, such as a surgical table rail. The present disclosure addresses one or more of the deficiencies in the prior art.

SUMMARY

In one exemplary aspect the present disclosure is directed to a PIM holder for attaching a PIM device having a cable to a rail in a medical environment. The PIM holder includes a holster and a clamping device. The holster includes an open end sized to receive a PIM device and having a cable opening extending from the open end on a side adjacent the open end to a side opposite the open end. The clamping device is sized and configured to attach the holster to a rail. The clamping device includes a stationary jaw secured to the holster and a moving jaw disposed adjacent the stationary jaw. The stationary jaw and moving jaw form an opening that receives the rail in a lateral direction and forms a passage therebetween to capture the rail. An actuator is pivotable between an open position and a closed position to displace the moving jaw to open and close the clamping device.

In one aspect, the clamping device comprises a biasing system slidably associated with the stationary jaw and connected to the moving jaw in a manner that biases the moving jaw toward the stationary jaw.

In one aspect, the PIM holder further includes a rotation system disposed between the holster and the clamping device. The rotation system includes a first rotational element connected to the holster and a second rotational element connected to the clamping device, the first rotational element being rotatable relative to the second rotational element.

In another exemplary aspect the present disclosure is directed to a PIM holder for attaching a PIM device having a cable to a rail in a medical environment. The PIM holder includes a clamping device sized and configured to attach to a rail, the clamping device including a clamp member having a first jaw and a second jaw, a cam member associated with the second jaw and configured to clamp a rail against the first jaw, and a hanger pivotably connected to clamp member, the hanger having a connecting portion formed therein. The PIM holder also includes a holster pivotably attached to the connecting portion of the hanger and configured to pivot in a roll direction substantially perpendicular to the pitch direction. The holster includes an open end sized to receive a PIM device and has a cable opening extending from the open end on a side adjacent the open end to a side opposite the open end, the holster interfacing with the hanger.

In another exemplary aspect the present disclosure is directed to a method of clamping a PIM holder for a PIM device having a cable to a rail in a medical environment. The method includes pivoting an actuator to open a clamping device by linearly displacing a moving jaw away from a stationary jaw to place the clamping device in an open condition, and introducing a rail between the stationary jaw and the moving jaw in a lateral direction so that a holster carried by the clamping device hangs from the rail. The holster may have an open end sized to receive a PIM device and may have a cable opening extending from the open end on a side adjacent the open end to a side opposite the open end. The method also includes releasing the actuator so that a biasing system linearly displaces the moving jaw toward the stationary jaw to capture the rail between the stationary and moving jaws.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
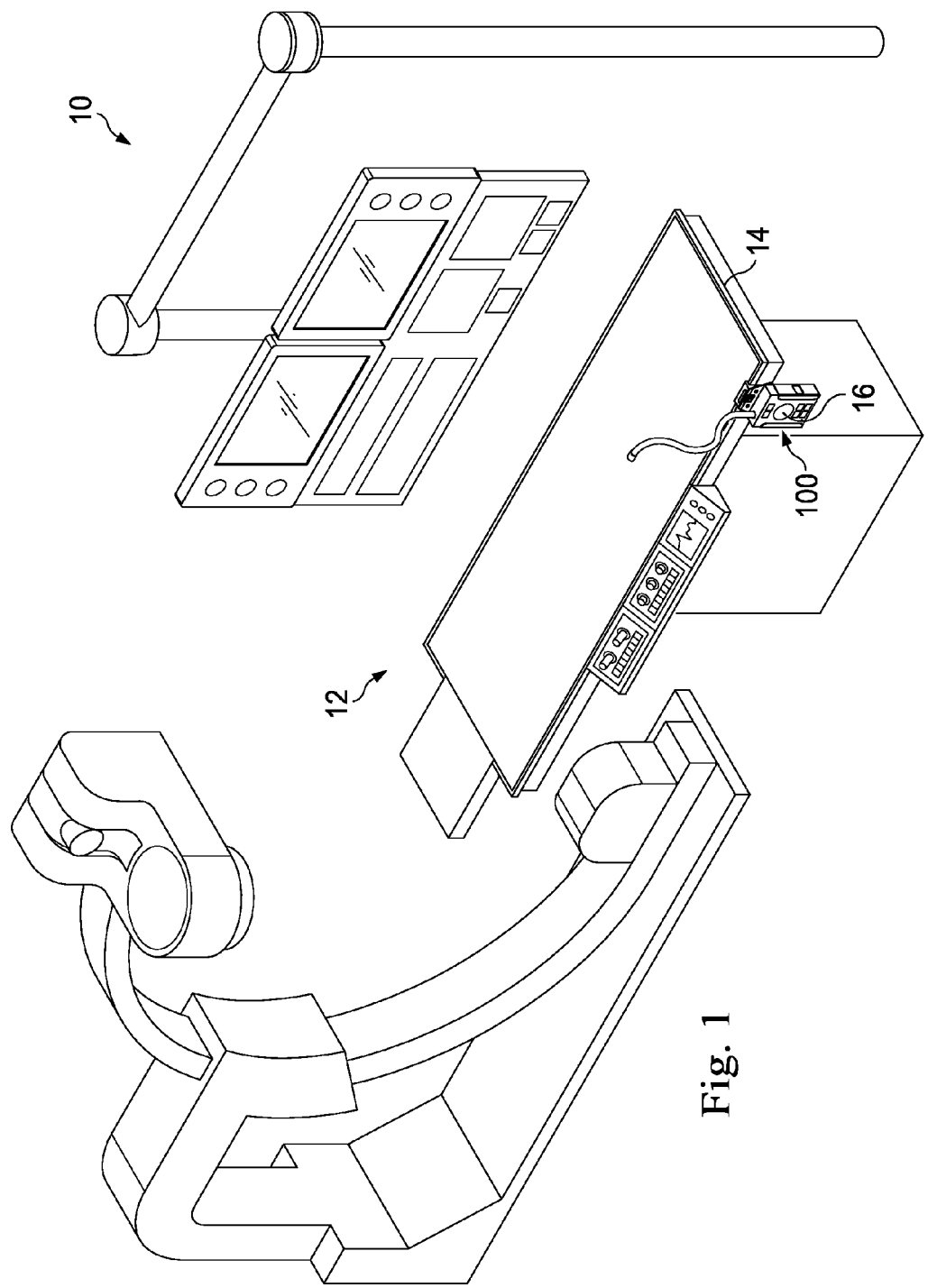
FIG. 1 is an illustration of an exemplary catheter lab system.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact. Furthermore, the following paragraphs describe many different embodiments of PIM holders with clamping devices. For the sake of ease of understanding, descriptions set forth with respect to one embodiment are understood to apply to other embodiments.

The present disclosure is directed to a PIM holder with a clamping system for a patient table that may be easily adjusted or moved to an orientation desired by a surgeon. It may be adjusted using only one hand, and does not require special tools. It can be adjusted more quickly than conventional knob-screw devices, and still provides a strong stabilizing foundation for holding surgical accessories. During procedures, the PIM holders may be easily readjusted to another location on the table. Because of its easily adjustable characteristics, the PIM holders disclosed herein may make surgical processes easier to accomplish, without requiring the surgeon to work around the PIM holders, but making it so that the surgeon can easily adjust them, thereby providing easier access to the patient, more convenient relocation of the PIM holders, speeding the process of accessory reorientation, and possibly contributing to a better patient outcome.

FIG. 1 shows an embodiment of a catheter lab system 10 including a patient table 12 having a side rail 14 disposed thereon. The catheter lab may also include a patient interface module (PIM) 16 adapted to hold a catheter having an imaging probe located near a distal end, a control panel, a monitor for displaying images and patient data, and a processing unit. Attached to the side rail 14, the operating system may include a PIM holder 100 that receives and holds the PIM in a location convenient for the medical staff using the catheter lab system 10.

The rails in this example are rectangular shaped in cross-section, however rails of other shapes are contemplated. For example, some rails are cylindrical or square shaped. Some IV poles are used as rails. Rails may be of any size, and in one example, the rails are with a height of about 1 inches and a width in the range of about ⅜ inch, although other sized rails are contemplated.

Figure 2:
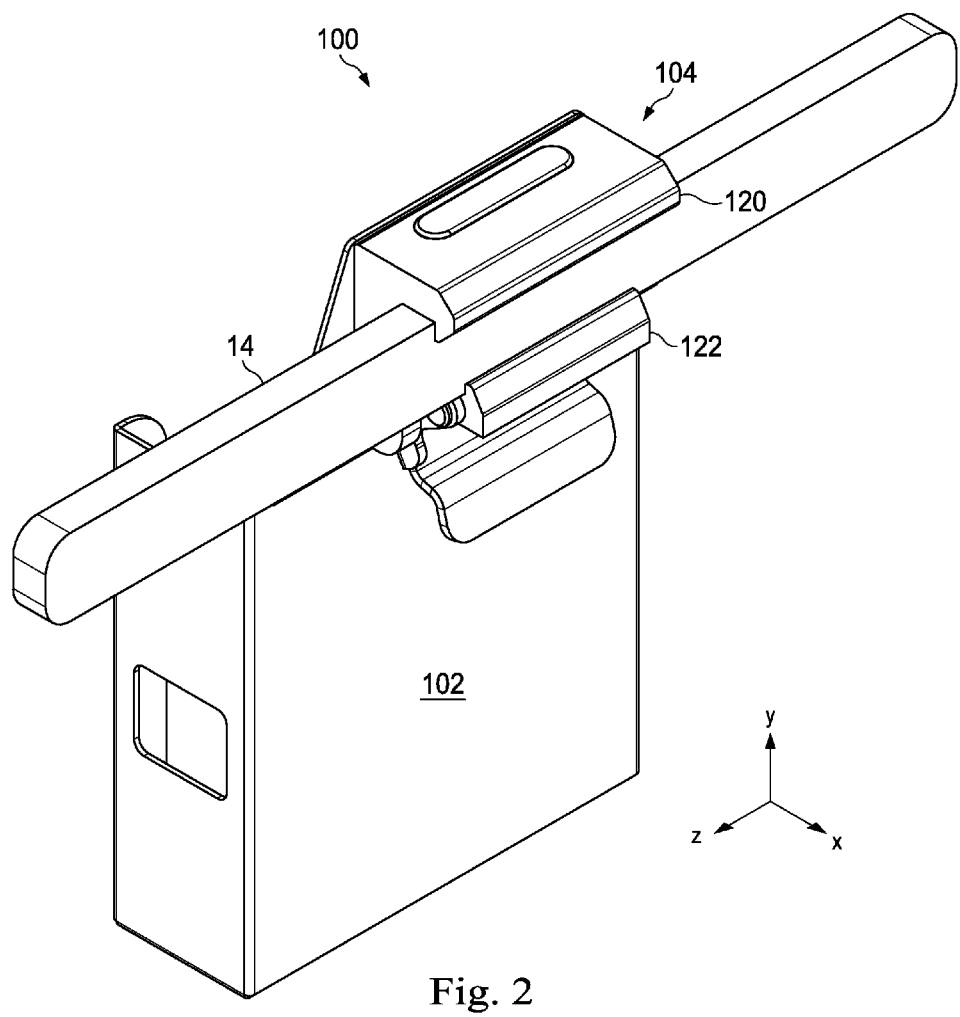
FIG. 2 is an illustration of an exemplary PIM holder according to an exemplary aspect of the present disclosure with a rail.
Figure 3:
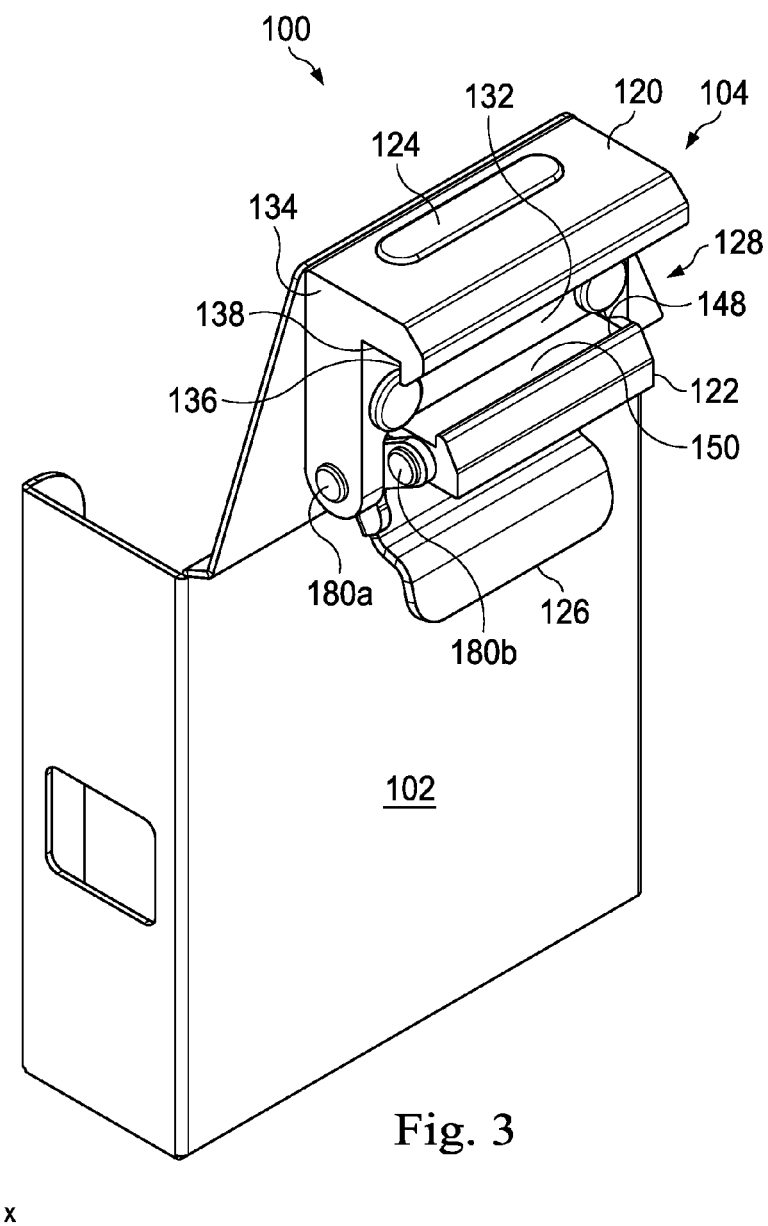
FIG. 3 is an illustration of an exemplary PIM holder according to the exemplary aspect of FIG. 2 without the rail.
Figure 4:
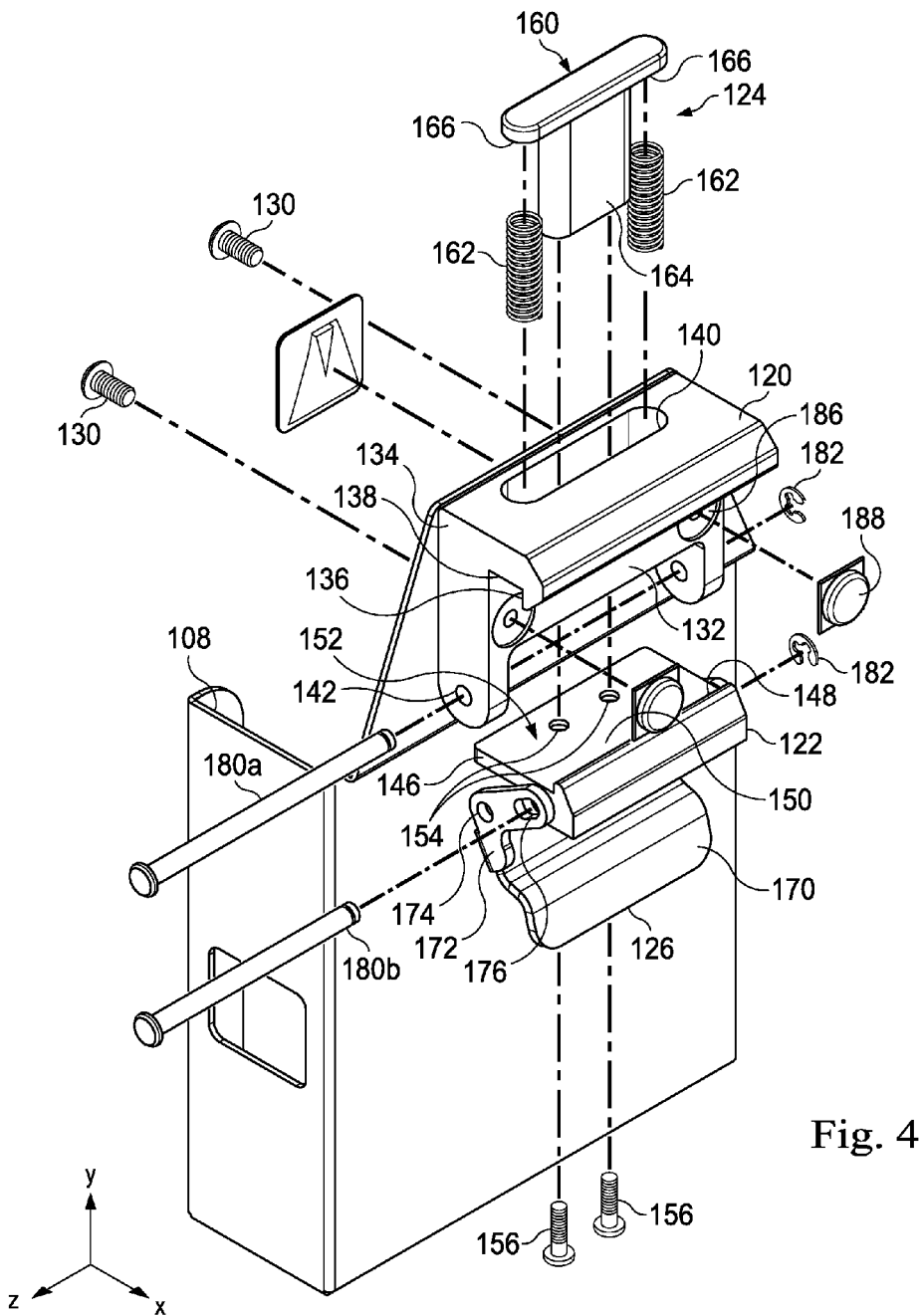
FIG. 4 is an illustration of an exploded view of the exemplary PIM holder according to the exemplary aspect of FIG. 2.
Figure 5:
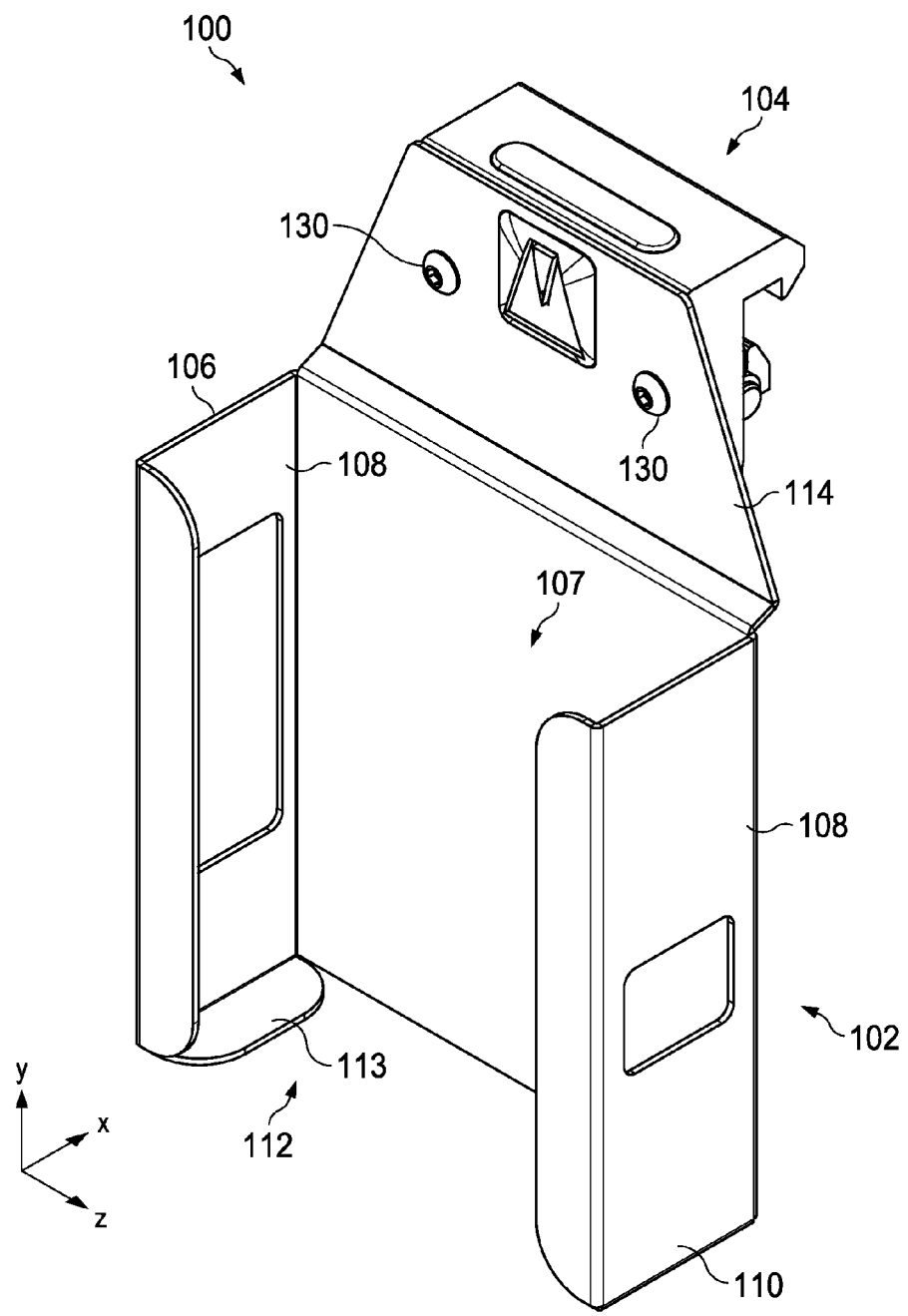
FIG. 5 is an illustration of another view of the exemplary PIM holder according to the exemplary aspect of FIG. 2.

FIGS. 2-6 show the PIM holder 100 in greater detail. The PIM holder 100 comprises a holster 102 and a clamping device 104 that is attachable to the rail 14 as shown in FIG. 2. With reference to FIG. 5, the holster 102 is a rigid device having a receiving end 106 with a receiving opening 107 sized to receive a PIM, sides or supports 108 configured to capture and retain the PIM therein, and a cable end 110 having a cable opening 112 sized to permit passage of a PIM cable (not shown). The cable opening is arranged to extend from the receiving opening 107 through the bottom of the holster 102. In this way, a PIM with a cable extending from its bottom can be held above the holster so that the cable laterally enters through the cable opening 112, and then the PIM may be lowered into and seated in the holster 102. In this embodiment, the holster 102 includes inwardly extending bottom tabs 113 that define the cable opening 112 and prevent through-passage of a PIM that is disposed in the holster 102. The holster in FIG. 5 is formed of a sheet metal bent to create the holster. However, other embodiments are molded or formed via other manufacturing techniques. In this example, the holster includes a rigid hanger tab 114 disposed adjacent the opening and configured to carry the clamping device 104.

The PIM holder may be sized, in one example, to receive a PIM. PIM are frequently sized with a width in the range of 1.5-3 inches, and a thickness of about 0.4-3 inches, and a height in the range of about 3-7 inches. Accordingly some embodiments of the PIM holsters have a receiving opening between 3 and 5 inches wide and with a thickness of between 1.5-3 inches. The cable opening may have a width in the range of about 0.25 inch or greater. Other sizes are contemplated.

The clamping device 104 receives and clamps onto the rail 14 that may be a rail on the patient table of the catheter lab system 10 discussed above. FIG. 2 shows the PIM holder 100 with the clamping device 104 connected to the rail 14, FIG. 3 shows the PIM holder 100 without the rail 104, FIG. 4 shows the clamping device in an exploded condition. FIG. 5, mentioned above, shows a front view of the holder 102 of the PIM holder 100.

Referring to FIG. 3, the clamping device 104 includes a stationary jaw 120, a moving jaw 122, a biasing system 124, and an actuator 126. As will be explained below, the stationary jaw 120 and the moving jaw 122 together form an opening 128 that is sized and configured to receive and capture a rail, such as the rail 14. In the embodiments shown, the stationary jaw 120 is fixed in place relative to the holster 102 by attachment elements, shown as fasteners or screws 130. These extend through the holster 102 into receiving holes in the stationary jaw 120.

The stationary jaw 120 includes a back structure 132 forming the backside of the opening 128 and an extending portion 134 forming a top portion of the stationary jaw 120. The top portion 134 includes a lip 136 that in cooperation with the top portion 134 and back structure 132, forms a laterally extending seat 138 that receives and secures the rail 14 in place. A biasing slot 140 extends into the top portion of the back structure 132 of the stationary jaw 120 and is shaped to receive the biasing system 124. Pivot holes 142 are formed in sides of the stationary jaw.

The biasing slot 140 is a partial through hole. It has a first width, shown in FIG. 4 configured to receive the biasing system 124. However, within the back structure 132 of the stationary jaw, the biasing slot 140 has a step, similar to that of a counter bore. The central portion of the slot 140 therefore continues through, while there is a shoulder or step on each side of the through hole within the slot 140.

The moving jaw 122 includes base plate 146 and a lip 148. The base plate 146 includes a surface that abuts against the bottom of the stationary jaw 120. As such, the back structure 132 of the stationary jaw, the base plate 146, and the lip 148 together form a seat 150 that receives and captures the rail 14. The base plate 146 includes a connecting system 152 that attaches the moving jaw 122 to the biasing system 124. The connecting system 152 includes through holes 154 and fasteners 156, shown in this embodiment as a set of fastening screws.

The biasing system 124 is configured to fit within the biasing slot 140 of the stationary jaw 120 and includes a bracket 160 and biasing elements 162. In the embodiments shown, the bracket 160 is a T-shaped structure having a body 164 and extending arms 166. The body 164 is configured to extend into the biasing slot 140 and through the through hole of the biasing slot 140. A bottom portion of the body 164 abuts the base plate 146 of the moving jaw 122. The fasteners 156 connect the base plate 146 to the body 164 of the biasing system 124.

The biasing elements 162 are disposed between the arms 166 and the shoulders or steps within the biasing slot 140. These biasing elements are shown in FIG. 4 as coils springs, although other biasing elements may be used. The biasing elements 162 bias the bracket 160 in the direction out of the biasing slot 140, away from the moving jaw 122. Since the moving jaw 122 is connected to the bracket 160, so doing also biases the moving jaw 122 toward the stationary jaw 120. Therefore, the clamping device 104 is biased to a closed or clamped position. This reduces the likelihood of inadvertent removal of the rail 14 from the clamping device 104. A displacement passage (formed through the moving jaw 122 in FIG. 4 behind the slot 176) extends laterally through the moving jaw 122. As discussed below, the displacement passage is used to displace the moving jaw 122 relative to the stationary jaw 120.

The actuator 126 includes a handle 170 and a plurality of lever arms 172. In the embodiment shown, the handle 170 and the lever arms 172 are formed from a single piece of sheet metal. In other embodiments, the handle and lever arms are connected to each other via welding, and adhesive or other attachment method, or they may be machines from a single component, may be molded together, or otherwise formed of a single monolithic piece. The handle 170 is configured to be actuated by a health care provider to open the clamping device 102 in order to attach or remove the PIM holder 100 from the rail 14.

The lever arms 170 include a pivot hole 174 and a sliding slot 176. The pivot hole 174 aligns with the pivot holes 142 in the stationary jaw 120. A pivot pin 180a, shown here as a clevis pin, extends through the pivot holes 142 and 174 and acts as an axle to define a pivot axis and allows the actuator 126 to pivot about the pin 180a relative to the stationary jaw 120. The sliding slot 176 aligns with the displacement passage on the moving jaw 122. A displacement pin 180b shown as a clevis pin extends through the sliding slot 176 and through the displacement passage, connecting the moving jaw 122 to the lever arms 170. Washers 182 connect to ends of the clevis pins 180 and prevent removal from the jaws 120, 122. The actuator 126 may be configured so that the handle 170 extends at an oblique angle from the clamping device 104 and the holster 102. This enable easy, one hand clamping and release to a rail 14. Although FIG. 4 shows the lever arms 172 disposed within the stationary jaw 120, other embodiments have the lever arms 172 disposed on the outside of the stationary jaw 120.

In the example shown in FIGS. 2-6, the back structure 132 includes spot faces 186 configured to receive compressible bumpers 188. These compressible bumpers 188 may be formed of a foam, elastomeric, or other compressible material and may permit snug and secure clamping of rails of different sizes. While shown on the back structure 132, other embodiments, include the compressible bumpers at other location on the clamping device, including in the seats 138, 150.

In use, a health care provider may use a single hand to attach or detach the PIM holder 100 to a rail, such as the bed rail 14. A health care provide may press the handle 170 so that it pivots about the clevis pin 180a. As it does so, the pivoting lever arm 172 forces the clevis pin 180b and the moving jaw 122 downward. As the rotation occurs, the clevis pin 180b slides along the sliding slot 176. Since the bracket 160 is fixed to the moving jaw 122, the bracket 160 moves downward, against the biasing force of the biasing elements 162. This opens the clamping device 104 enabling it to be placed on a rail, such as a bed rail or other structure. When the rail enters the opening 128, it may abut the compressible bumpers 188. Depending on the size, it may compress the bumpers. The rail may be seated in one of the seats 138, 150. To attach the PIM holder 100 to the rail, the health care provider needs only to release the handle 170. The biasing elements 162 then bias the bracket 160 upward, which carries the moving jaw 122 toward the stationary jaw 120 until the rail is seated in both the seats 138, 150 or until the moving jaw 122 comes into contact with the stationary jaw 120, thereby capturing the rail within the clamping device 100.

If during the medical procedure, it becomes desirable to move the PIM holder 100, the holder 100 can be simply opened with one hand and slid along the rail or may be removed from the rail and reattached in a different location. Although the actuator 126 pivots relative to the stationary and the moving jaws 120, 122, the jaws linearly translate relative to each other, and do not pivot relative to each other.

Figure 6:
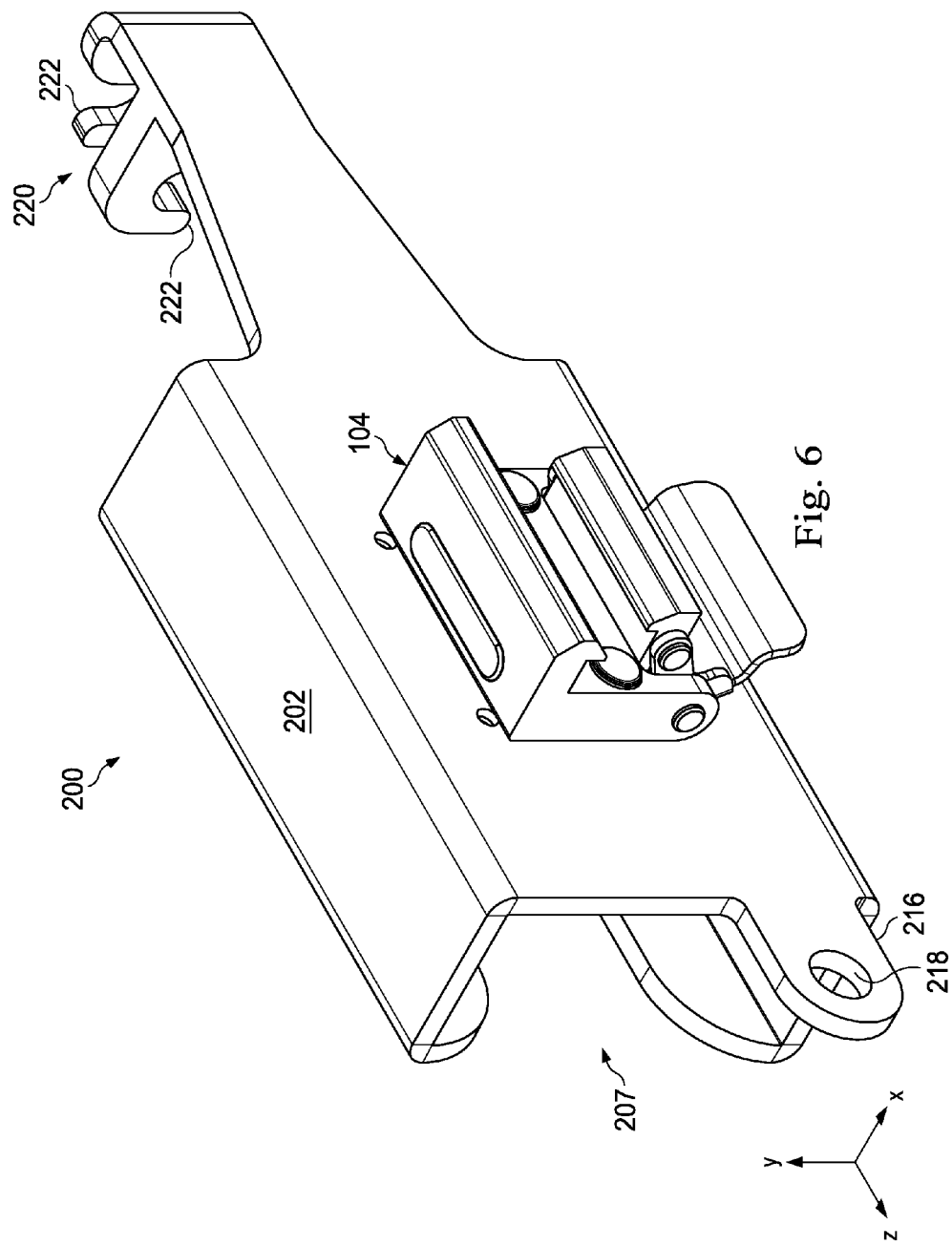
FIG. 6 is an illustration of an exemplary PIM holder according to an exemplary aspect of the present disclosure.
Figure 7:
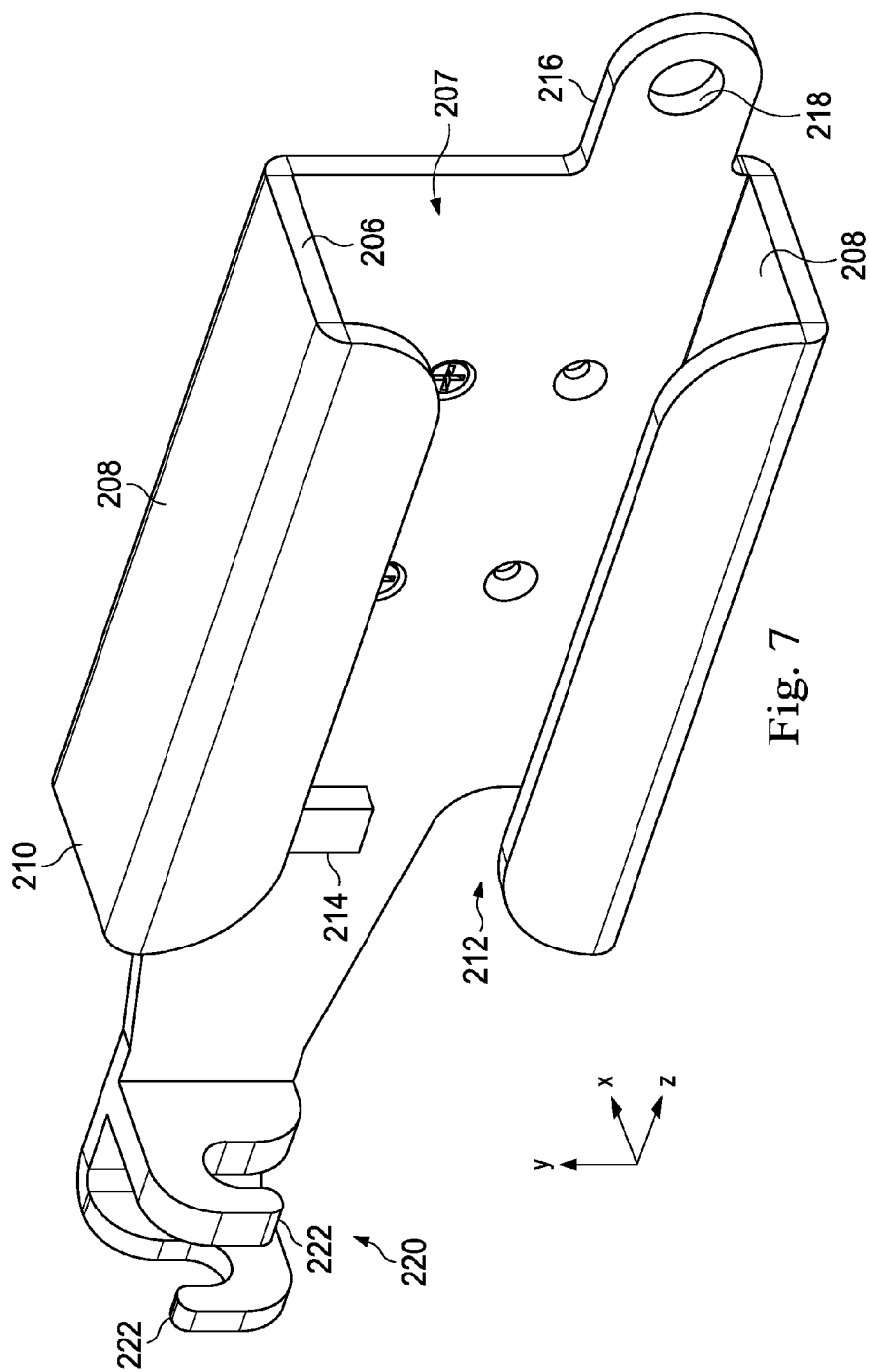
FIG. 7 is an illustration of another view of the exemplary PIM holder according to the exemplary aspect of FIG. 6.

FIGS. 6 and 7 show an alternative PIM holder 200. The PIM holder 200 includes a holster 202 and the clamping device 104. The holster 202 includes a receiving end 206 with a receiving opening 207 sized to receive a PIM, sides or supports 208 configured to capture and retain the PIM therein, and a cable end 210 having a cable opening 212 sized to permit passage of a PIM cable (not shown). In this embodiment, the holster 202 also includes a stop element 214 disposed in a manner to limit how far the PIM may be inserted into the holster. A tab 216 adjacent the receiving end 206 has a through hole 218 to permit hanging from an IV pole or other equipment commonly found in medical treatment rooms. Its worth noting that any of the holsters disclosed herein may include such a tab and system for hanging as an alternative to clamping onto a rail. Here, the cable opening 212 also includes a cable support 220 that includes two spaced, and opposing hooks 222 that cooperate to secure the PIM cable in place.

In this embodiment, the holster 202 is aligned with the clamping device so that the receiving end 206 of the holster 202 is aligned on its side, or parallel to the direction of a rail when the PIM holder 200 is disposed on a rail.

Figure 8:
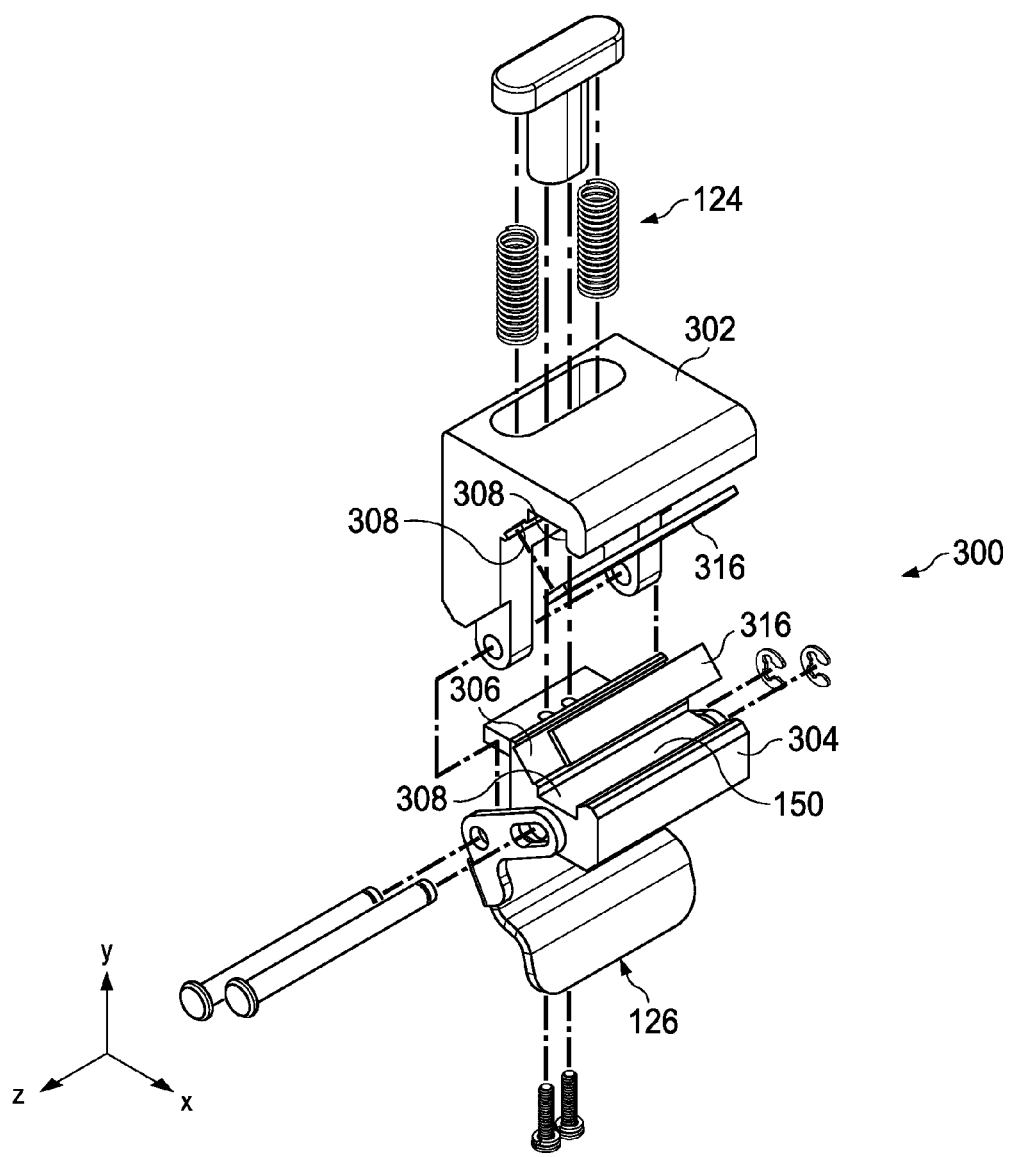
FIG. 8 is an illustration of an exemplary clamping device in an exploded view usable with a PIM holder according to an aspect of the present disclosure.
Figure 9:
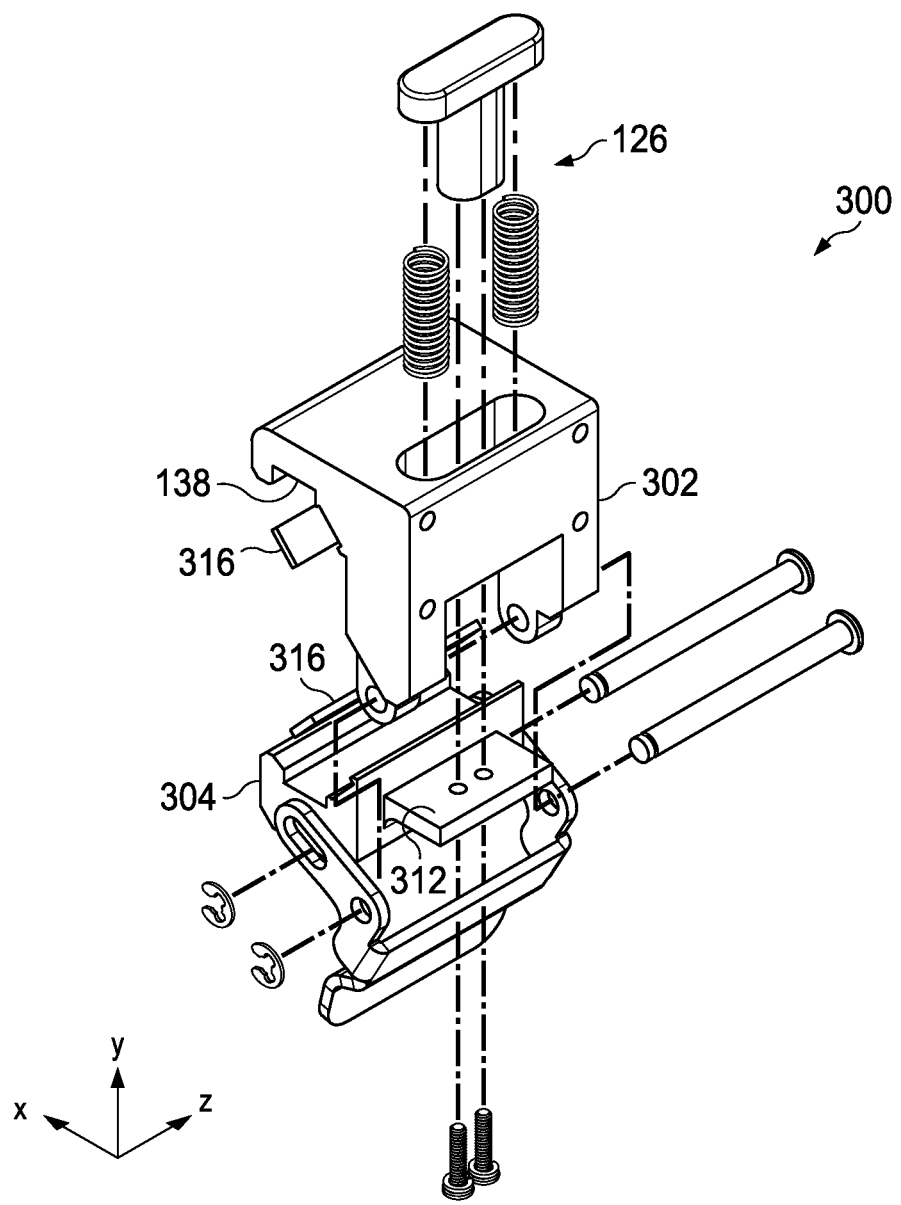
FIG. 9 is another illustration of an exploded view of the exemplary clamping device of FIG. 8 usable with a PIM holder according to an aspect of the present disclosure.
Figure 10:
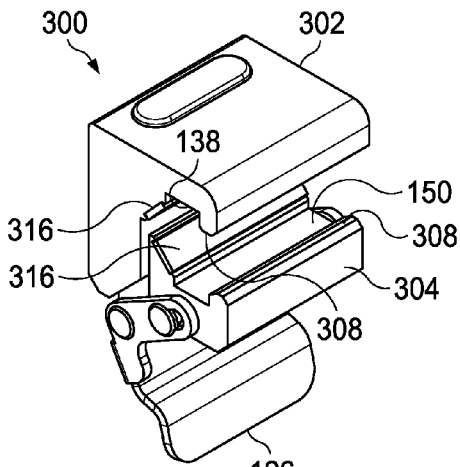
FIG. 10 is an illustration of the exemplary clamping device of FIG. 8 usable with a PIM holder according to an aspect of the present disclosure.

FIGS. 8-10 show an additional embodiment of a clamping device, referenced herein by the numeral 300. The clamping device 300 may be connected to any PIM holster described herein. The clamping device 300 differs from the clamping device 104 because it is arranged to connect to either a rectangular rail as described above or a cylindrical rail, such as, for example, an IV pole. The general operation of the clamping device 300 is similar to that described above, and it will not all be repeated here. The clamping device 300 does have a different form that enables it to secure to a cylindrical rod. For example, the clamping device 300 includes a stationary jaw 302 and a moving jaw 304. Here the stationary jaw 302 and the moving jaw 304 each include angled surfaces 306 that form a seat for the cylindrical rails. For example, they each include a lip 308 that is chamfered and includes an angled engagement surfaces. Because of the angled engagement surface the overall structure of the moving jaw is modified as can be seen in the back view shown in FIG. 9. Here, the moving jaw 304 includes a base plate 312 that extends from a body structure designed to support the engagement surface of the moving jaw 304. High friction elements 316, such as elastomeric elements, may form the interfacing surfaces of the jaws and may be configured to engage a rail captured in the jaws.

Figure 11:
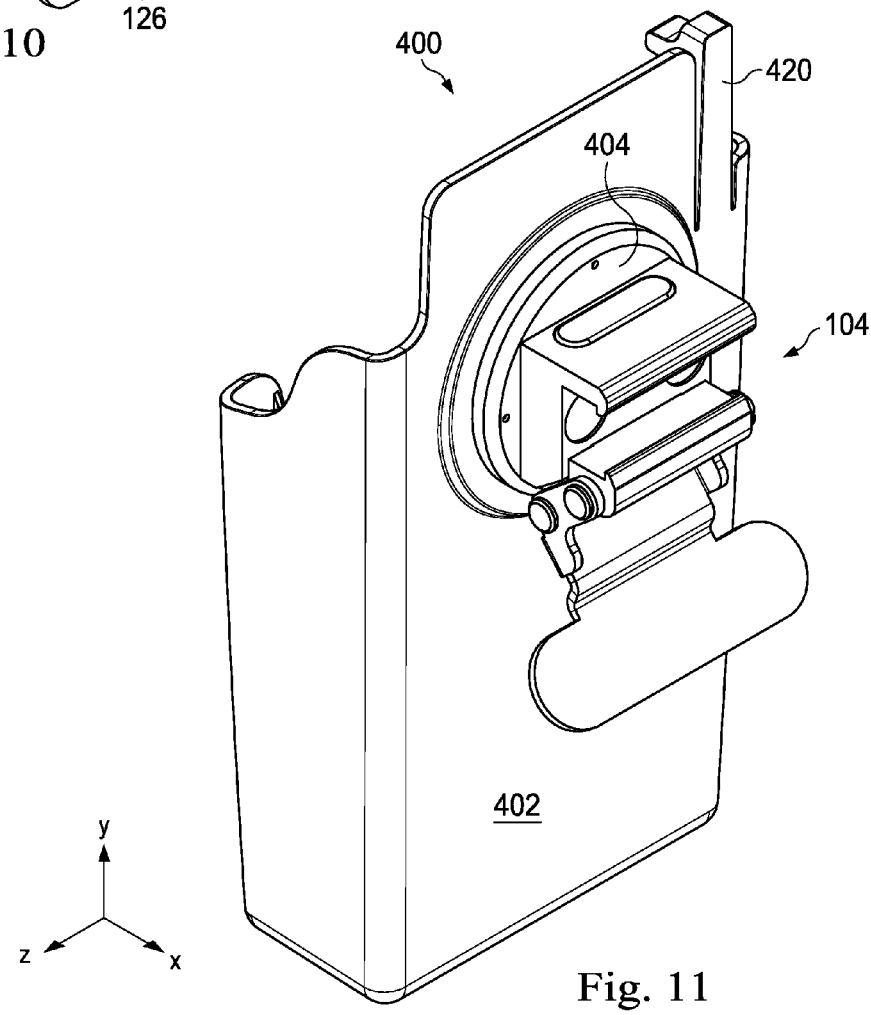
FIG. 11 is an illustration of an exemplary PIM holder according to an exemplary aspect of the present disclosure.
Figure 12:
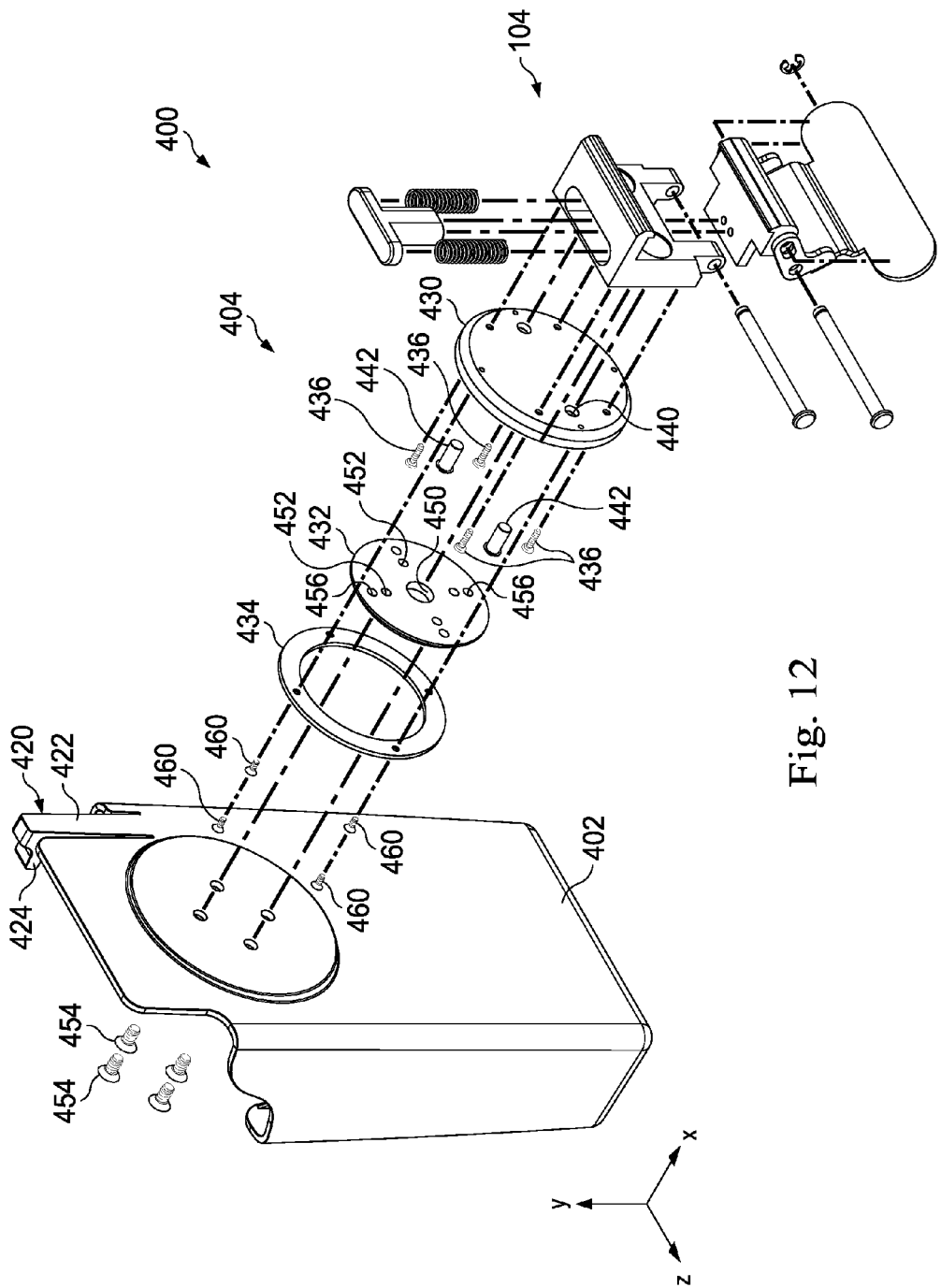
FIG. 12 is an illustration of an exploded view of the exemplary PIM holder according to the exemplary aspect of FIG. 11.
Figure 13:
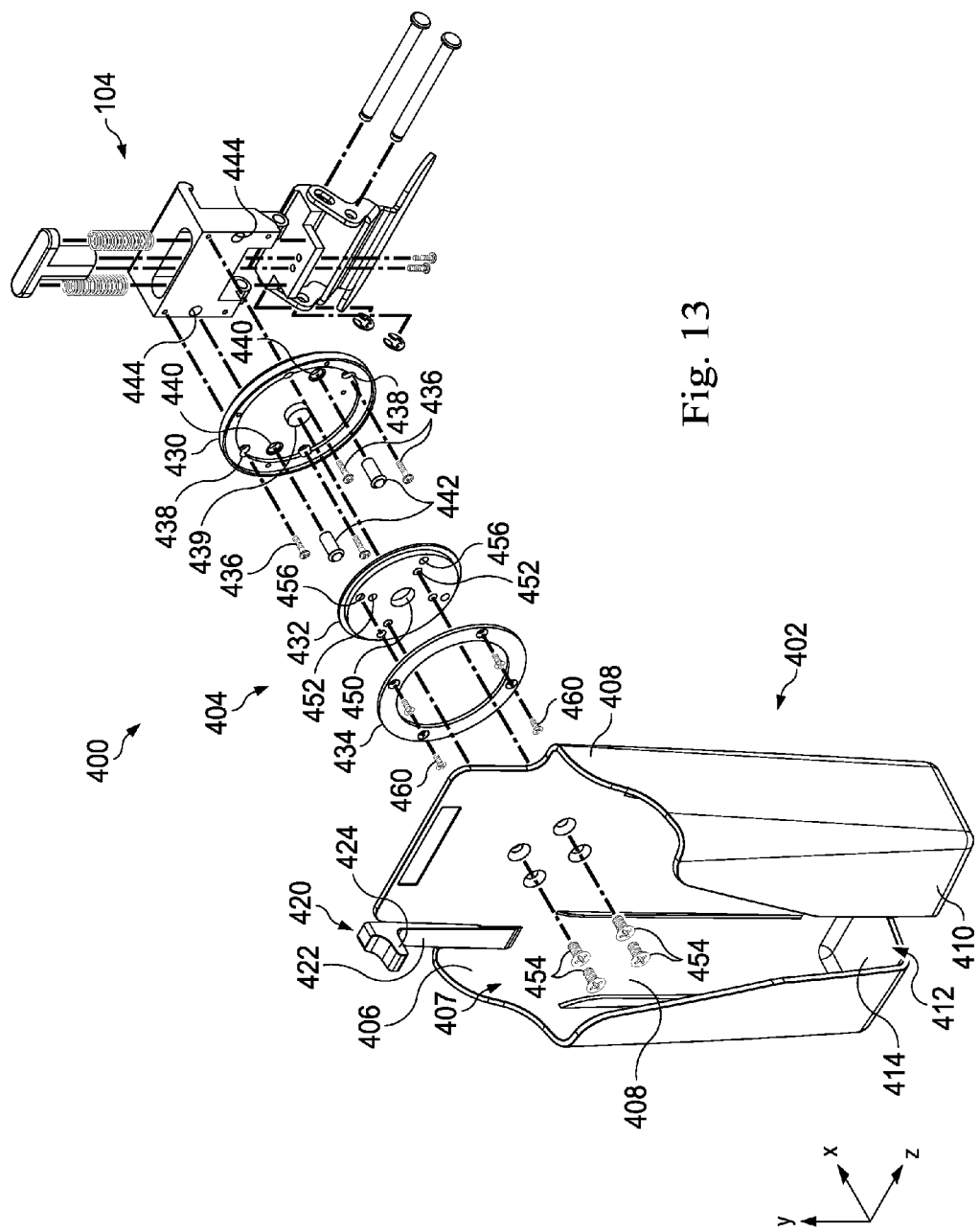
FIG. 13 is an illustration of an exploded view of the exemplary PIM holder according to the exemplary aspect of FIG. 11.

FIGS. 11-13 show an alternative PIM holder 400. The PIM holder 400 includes a holster 402, the clamping device 104, and a rotation mechanism 404. As will become apparent below, the rotation mechanism permits rotation of the holster 402 so that the PIM can be hung on a rail in any desired orientation.

The holster 402 includes a receiving end 406 with a receiving opening 407 sized to receive a PIM, sides or supports 408 configured to capture and retain the PIM therein, and a cable end 410 having a cable opening 412 sized to permit passage of a PIM cable (not shown). In this embodiment, the cable opening is defined between two holster bottom portions 414, and the cable opening forms a part of the overall opening connection the receiving end and the cable opening. This embodiment includes a locking tab 420 flexibly forming a part of the holster 402. The locking tab 420 includes an elastically deformable finger 422 and a stop piece 424. The locking tab 420 is sized and positioned to prevent the PIM from falling from the holster 402 even if the holster 402 is rotated to its side or upside down. In this example, the finger 422 of the locking tab 420 may elastically deflect to permit the PIM to be inserted into the opening, and the tab 420 may then elastically return to its original position. In this position, the stop piece 424 may extend over the PIM and mechanically prevent the PIM from inadvertent removal from the holster.

The rotation mechanism 404 comprises a housing 430, a rotating plate 432, and a retention ring 434. The housing 430 is configured to connect directly to the clamping device 104 via fasteners 436. It includes four spaced fastening holes 438 that receive the fasteners 436, and the fasteners extend into corresponding holes in the stationary jaw 120 of the clamping device 104. In addition, the housing includes a central boss 439 and a two detent holes 440 extending therethrough. Detent pins 442 pass through the detent holes 440, and in this embodiment, extend into pin holes 444 formed in the stationary jaw 120. The detent pins 442 have rounded tips that interface with the rotating plate 432.

The rotating plate 432 includes a central hole 450 that receives the boss 438 and maintains the rotating plate in a central position relative to the housing 430. The rotating plate 432 includes four fastener holes 452 that receive fasteners 454 that connect the rotating plate 432 to the holster 402. Four detent holes 456 are disposed in the plate in a position that allows them to align with the detent pins 442. The holes 456 may be through holes, or may be dimples that receive the detent pins 442. In this embodiment, the detent holes 456 are spaced 90 degrees apart. However, other spacing arrangements are contemplated.

The retention ring 434 includes four fastener holes that receive fasteners 460 that connect the retention ring 434 to the housing 430. The retention ring 434 secures the rotating plate 432 within the housing 430 and prevents its removal.

In use, either before or after clamping the clamping device 104 to a rail, the rotation mechanism 404 permits a health care provider to rotate the holster 402 relative to the clamping device 104. By rotating the holster 402, the rotating plate 432 moves within the housing 430, which is fixed in place relative to the clamping device 104. As the rotating plate 432 rotates, the detent pins 442 engage and disengage the detent holes 456 on the rotating plate. Accordingly, the user is provided with tactical feedback indicating when the holster is rotated each 90 degrees. Furthermore, the detents provide increased friction to reduce inadvertent rotation of the holster 402 relative to the clamping device 104.

While two detents are shown, other embodiments include only one or more than two. Other embodiments include other detent systems. Some embodiments are configured to create an audible click when the detent is aligned with the detent pin. Other rotational systems are also contemplated.

Figure 14:
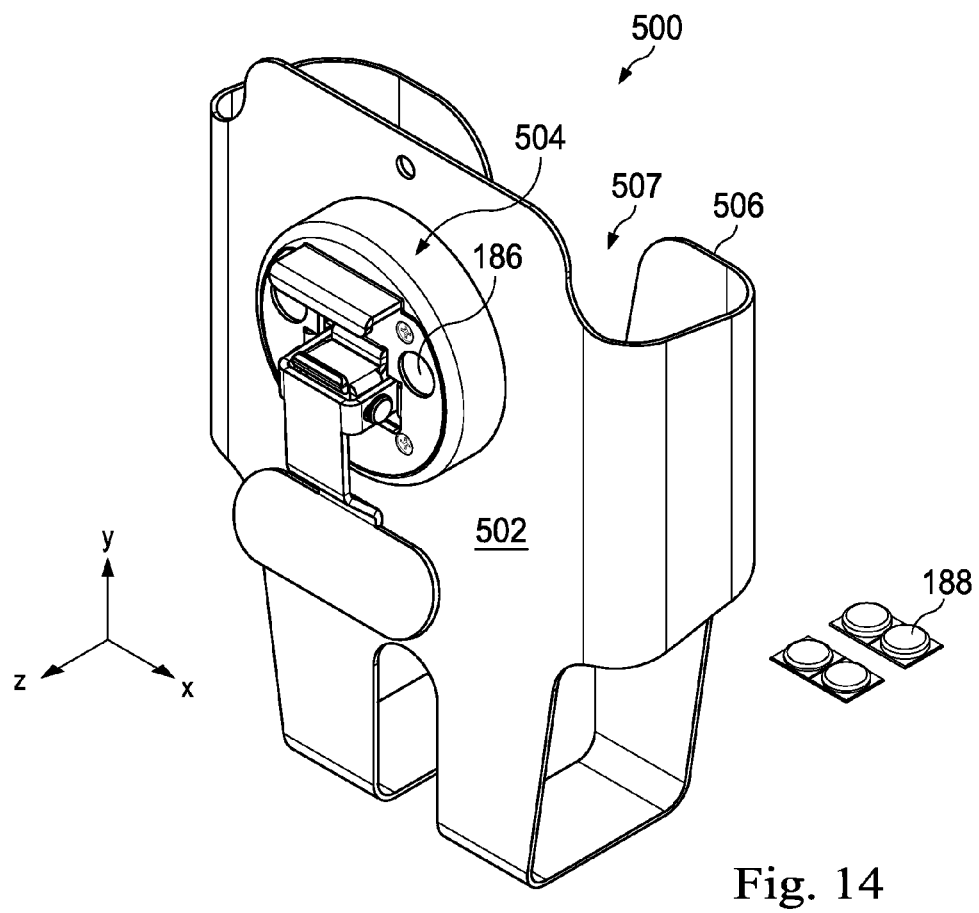
FIG. 14 is an illustration of an exemplary PIM holder according to an exemplary aspect of the present disclosure.
Figure 15:
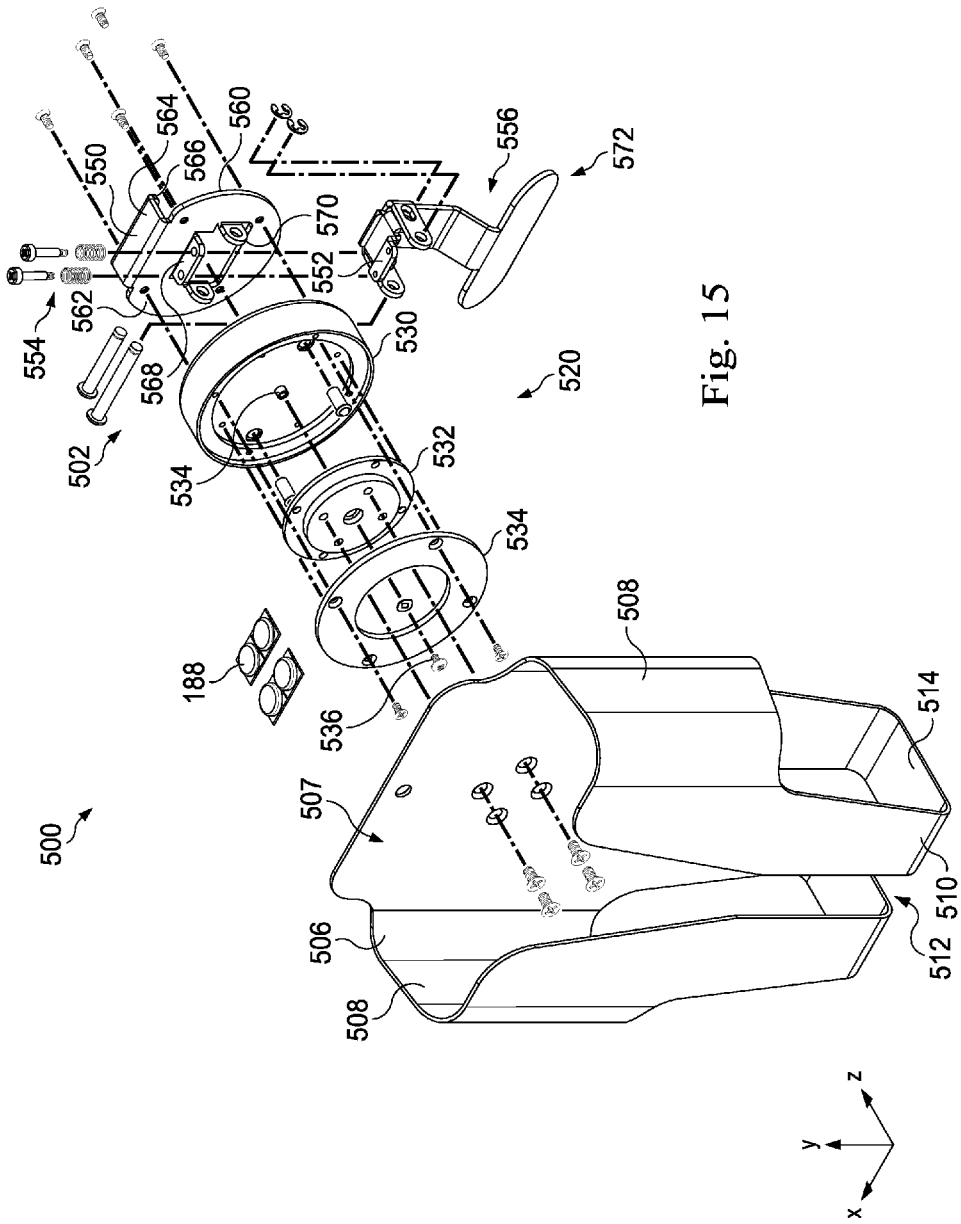
FIG. 15 is an illustration of an exploded view of the exemplary PIM holder according to the exemplary aspect of FIG. 14.
Figure 16:
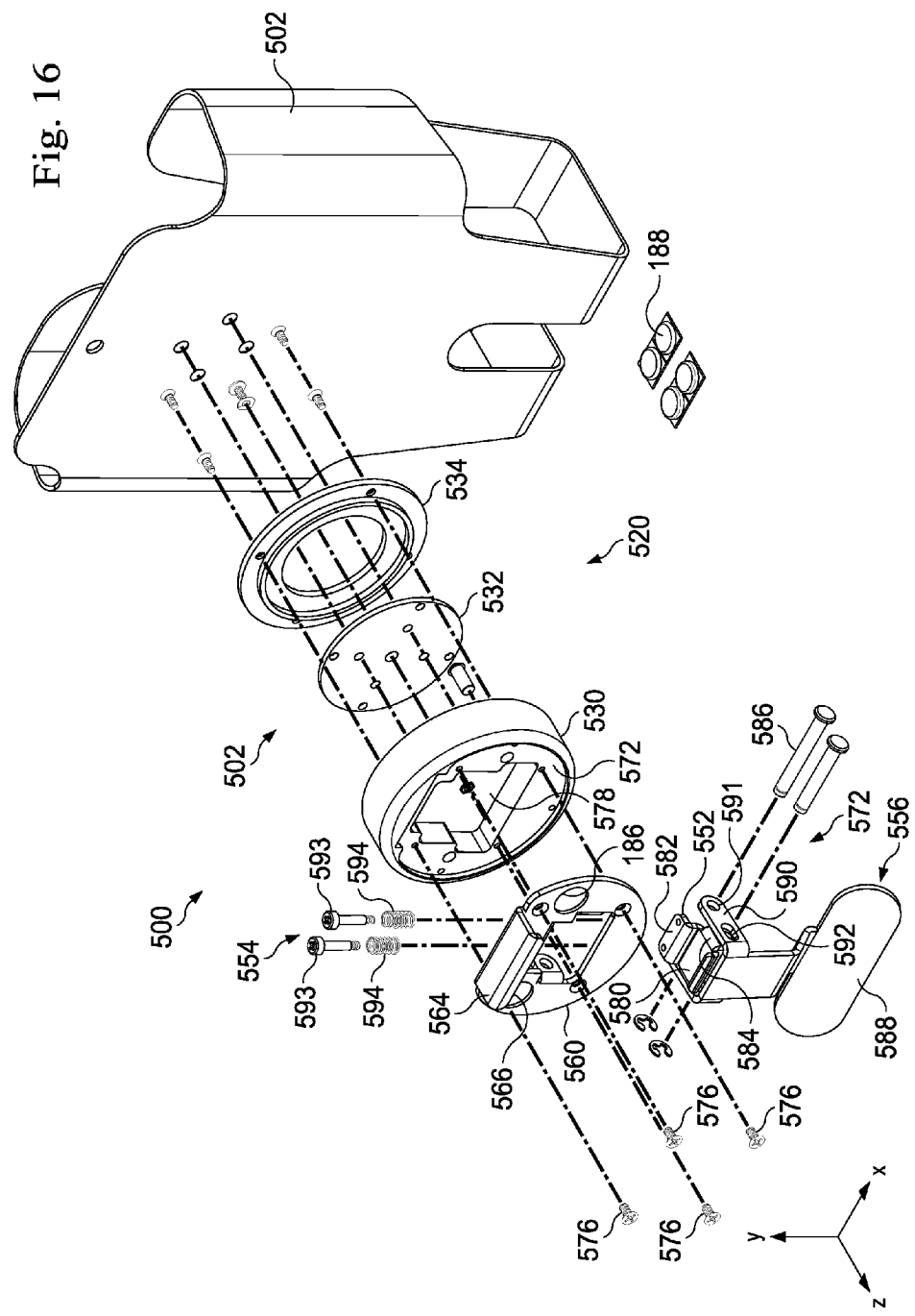
FIG. 16 is an illustration of an exploded view of the exemplary PIM holder according to the exemplary aspect of FIG. 14.

FIGS. 14-16 show another embodiment of a PIM holder 500. The holder includes a holster 502 and a clamping portion 504. In this embodiment, the clamping portion 504 comprises a more integrated rotational and clamping system. The holster 502 includes a receiving end 506 with a receiving opening 507 sized to receive a PIM, sides or supports 508 configured to capture and retain the PIM therein, and a cable end 510 having a cable opening 512 sized to permit passage of a PIM cable (not shown). A holder bottom 514 prevents the PIM from coming out the bottom.

The clamping device 502 includes a rotation mechanism 520 and a clamping device 522. The rotation mechanism 520 includes a housing 530, a rotating plate 532, and a retention ring 534. The rotation mechanism 520 is similar in many ways to the rotation mechanism 404 and the descriptions will not repeated in great detail. In this embodiment however, a fastener 536 secures the rotation plate 532 to the housing 530. The fastener 536 extends through the rotating plate 532 and into the boss 534 on the housing 530.

In this embodiment, the housing 530 is formed to receive a portion of the clamping device 522. The clamping device 522 includes a stationary jaw 550, a moving jaw 552, a biasing system 554, and an actuator 556. In this embodiment, the stationary jaw 550 is formed of a single sheet metal plate and is configured with a body 560 and with a back structure 562 and an extending portion 564 with a lip 566. Together these form a seat in the stationary jaw for the rail 14. The stationary jaw 550 also includes a tab 568 interfacing with the biasing system 554 and pivot tabs 570 in tabs used to pivotably connect the stationary jaw 550 to the actuator 556. The back structure 562 fits into a recess 572 in the housing 530 that is non-circular, and therefore, the stationary jaw 550 cannot rotate relative to the housing. The stationary jaw 550 is secured to the housing 530 via fastening elements 576 shown as screws.

The moving jaw 552 is also formed of a single sheet-metal piece and fits within a recess 578 the housing 530. It includes a base plate 580, bent to form a lip and that includes a connection portion 582 for connecting to the biasing system 554. Tabs 584 with holes are used to receive a pin 586 that connect the lower jaw 552 to the actuator 556.

The actuator 556 includes a handle 588 and a lever arm 590. The lever arm 590 includes pivot holes 591 and sliding slots 592. When assembled, the pivot holes 591 align with the pivot holes in the stationary jaw 550 and a pivot pin 586 extends therethrough. The sliding slots 592 align with holes in the moving jaw 552 that are connected by a pin.

The biasing system 554 in the embodiment includes attachment elements as screws 593 and biasing elements 594. The screws 593 extend through the biasing tab 568 on the stationary jaw 550 and into the moving jaw 552. Each screw 593 is associated with a biasing element 594 that biases the screw 593 away from the moving jaw 552, thereby pulling the moving jaw 552 toward the stationary jaw 550 in a manner that closes the clamping device. Here, the housing 530 has a recess sized to receive the biasing system. Spot faces 186 are configured to receive compressible bumpers 188. The overall operation of the rotation mechanism 520 and the clamping device 522 is similar to that described above and will not be repeated.

Figure 17:
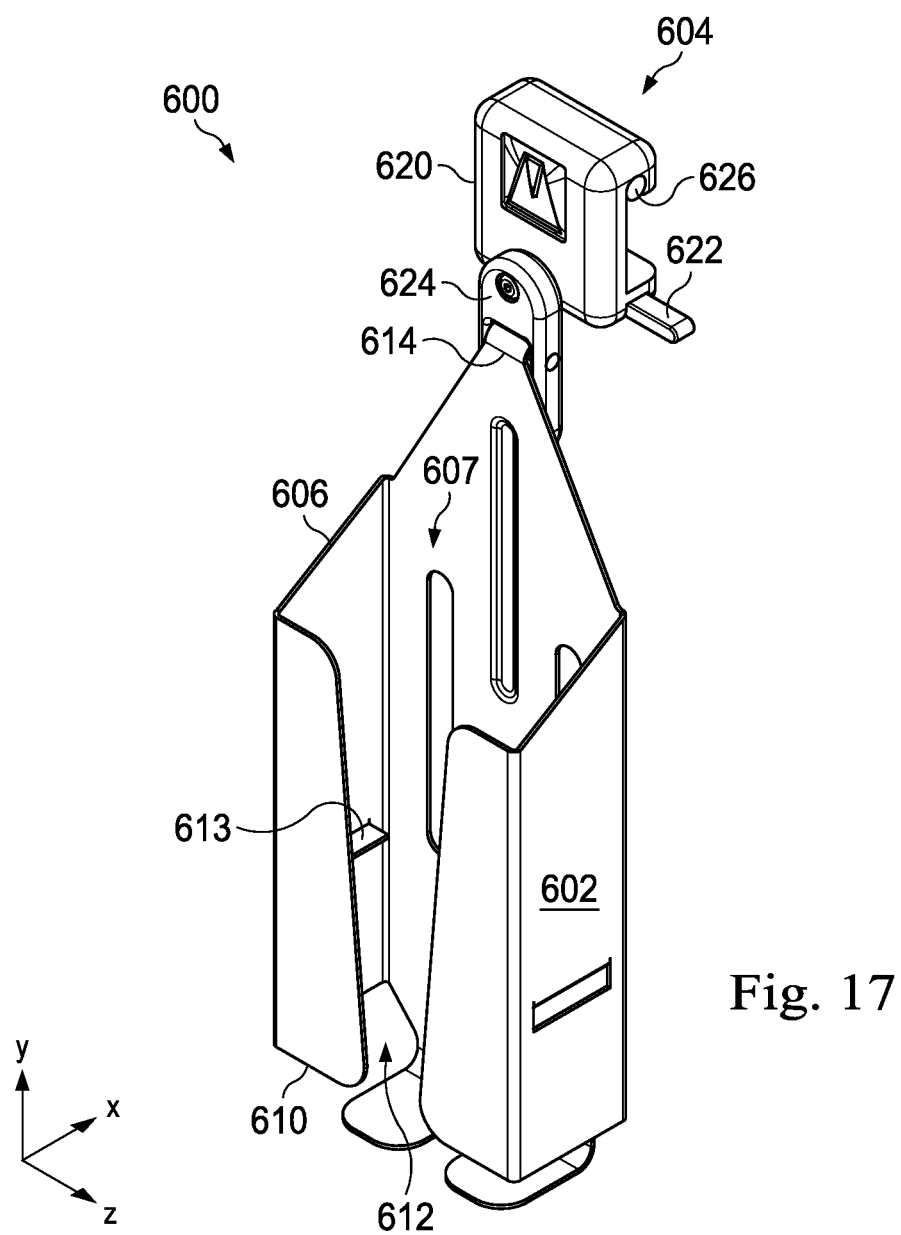
FIG. 17 is an illustration of an exemplary PIM holder according to an exemplary aspect of the present disclosure.
Figure 18:
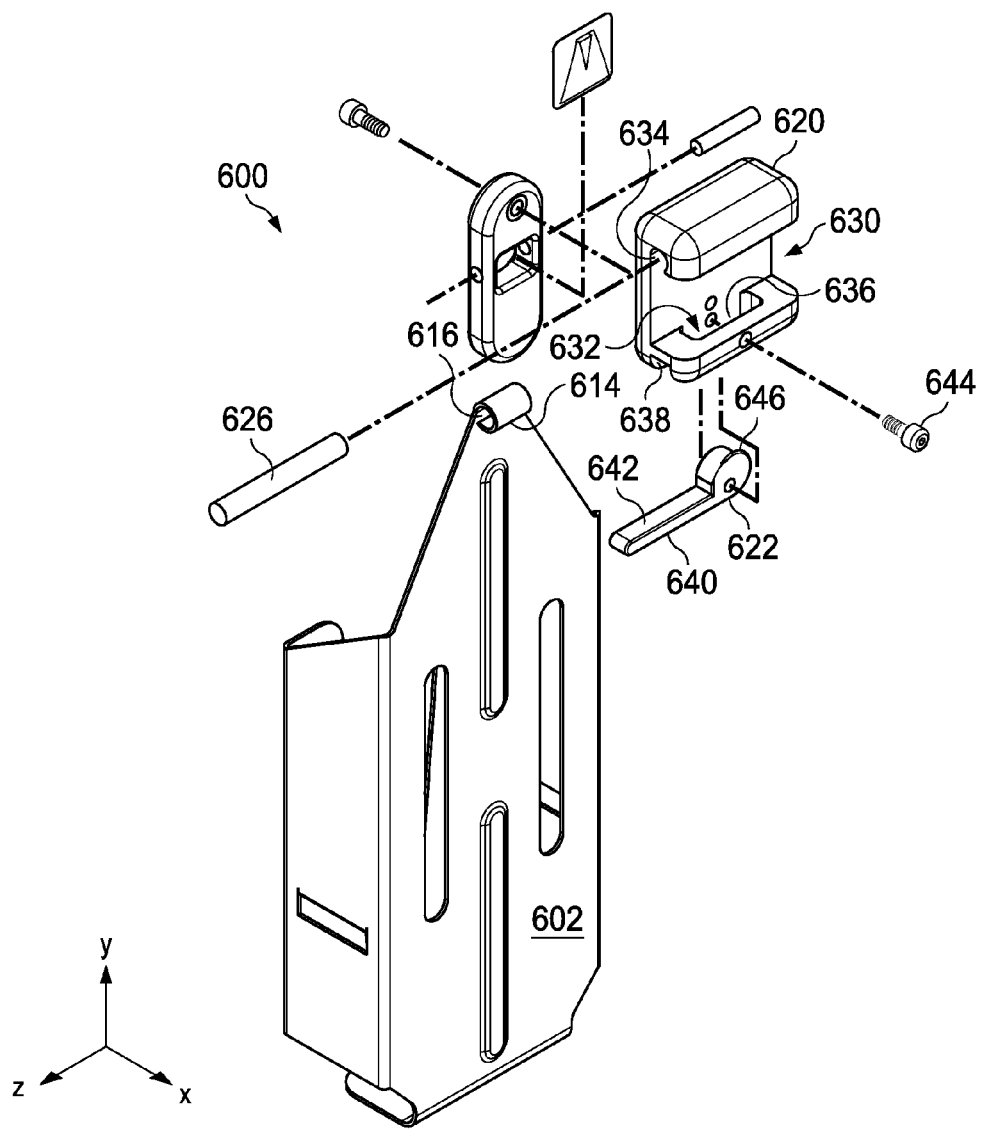
FIG. 18 is an illustration of an exploded view of the exemplary PIM holder according to the exemplary aspect of FIG. 17.
Figure 19:
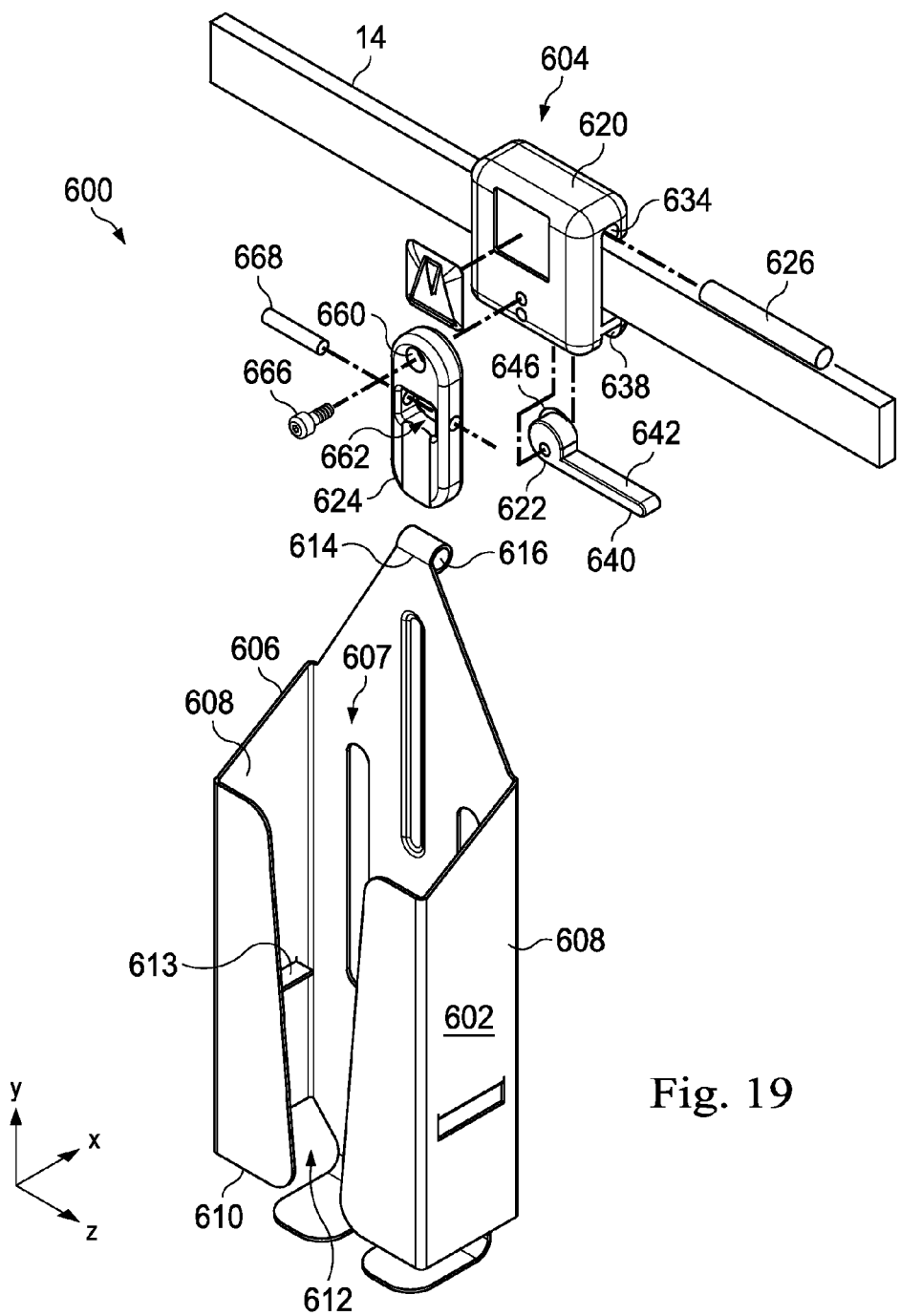
FIG. 19 is an illustration of an exploded view of the exemplary PIM holder according to the exemplary aspect of FIG. 17.

FIGS. 17-19 show an additional embodiment of a PIM holder 600. This embodiment includes a holster 602 and a clamping device 604. The holster 602 comprises a receiving end 606 with a receiving opening 607 sized to receive a PIM, sides or supports 608 configured to capture and retain the PIM therein, and a cable end 610 having a cable opening 612 sized to permit passage of a PIM cable (not shown). In this embodiment, the holster 602 includes inwardly extending tabs 613 disposed along the sides 608 that define the cable opening 612 and prevent through-passage of a PIM that is disposed in the holster 602.

The holster 602 includes a connector 614 configured to pivotably attach to the clamping device 604. In the example shown, the connector 614 is formed of a cylindrical passageway 616 that permits the holster to pivotably connect to the clamping device 604. The connector 614 is also disposed to be offset from a plane through the backwall of the holster. This offset allows the holster to pivot within a limited pivot range while cooperating with the clamping device 604 to prevent pivoting beyond the vertical range in one direction. In this example, where the holster is formed of a piece of sheet metal, the connector 614 is formed of metal rolled in a direction away from the side of the holster that receives the PIM.

The clamping device 604 receives and clamps onto the rail 14 that may be a bed rail for the catheter lab system 10 discussed above. The clamping device 604 includes a clamp body 620, a cam member 622, a hanger 624, and a cushion 626.

The clamp body 620 is a C-shaped member having a laterally extending passage 630 with an opening 632 to the passage 630 that receives the rail. The top of the passage 630 includes a laterally extending recess 634 formed along the length of the top passage that receives the rail, creating a lip that prevents inadvertent removal of the rail. The bottom of the passage 630 is formed as a flat surface extending from the opening into the passage 630 and has a through hole 636 therethrough, which receives the cam member 622. A lateral passage 638 along the outside of the clamp body intersects with the through hole 636 and is sized to receive a portion of the cam member 622.

The cushion 626 is disposed in the recess 634 in a position to engage a rail being inserted into the recess, behind the lip. The cushion 626 may be an elastomeric or foam bumper configured as a compressible surface against which the rail may be pressed. In this embodiment, it is a cylindrical-shaped bumper. In other embodiments, the cushion is shaped in other configurations. In addition to providing a cushion against which the rail may be pressed, the cushion also may provide a higher frictional resistance to lateral sliding, providing a more reliable holding force on the rail.

The cam member 622 comprises a cam 640 and a handle 642. The cam 640 is disposed in the through hole 636 and pivotably secured in place by a pivot pin 644 extending into the clamp body 620 and through the cam 640. Rotation of the cam 640 within the through hole 636 about the pivot pin 644 increases and decreases the distance between the cam 640 and the opposing recess 634 of the clamp body 620 in a manner that captures a rail within the clamping device 602. The cam 640 also includes a projecting side wall 646 disposed along the outer-facing side of the cam 640. The projecting side wall 646 is disposed in a location so that when the cam rotates and engages a rail, the side wall 646 physically blocks removal of the rail from clamp body 620, thereby securing the rail in place. Other embodiments have a lip along the bottom of the clamp body adjacent the clamp opening 632 that secures the rail in place.

The handle 642 extends from the cam is shaped and sized to provide simple one-hand operation. The handle 642 may be used to rotate the cam 640 about the pivot pin 644. When the clamping device 604 is in a closed position, the handle 642 is disposed within the lateral passage 638.

The hanger 624 hangs downward from the clamp body 620 and supports the holster 602. Because of its configuration, the hanger 624 provides side-to-side pivoting about pitch axis defined by a pivot point and provides rotation about a roll axis in a direction normal to the pitch direction. The hanger 624 includes a pivot hole 660 at a distal end and includes a centrally disposed connecting portion shown as a hole 662 for receiving the connector 614 of the holster 602. A pivot pin 666 attaches the hanger to the clamp body 620. The pivot pin 666 forms the pitch axis, providing pivoting substantially within a plane extending in a lateral direction. A roll pin 668 extends through sides of the hanger and through the centrally disposed hole. Since the holster 602 hangs from the roll pin 668, it may roll within a plane perpendicular to the pitch plane. In this embodiment, because the hole 662 is disposed central in the hanger instead of at its end, the roll angle is limited and the holster 602 is prevented from rolling underneath the clamp body 620. That is, the bottom portion of the hanger 624 acts as a rotation stop in the roll direction, preventing over rotation. Accordingly the holster 602 rolls in one direction from a position substantially perpendicular to a position. This limitation on the roll direction ensures that the holster does not swing into the patient table even if touched or bumped while a physician is treating a patient. This maintains a quieter and less disruptive surgical environment. Other embodiments have a greater range of movement about the roll axis.

Until clamped, the cam member 622 may hang freely from the pivot pin 644 in the cam body 620. With the cam member handle 642 hanging downward, the cam 640 is in a position permitting the introduction of a rail through the opening 632 and into the passage 630. The clamp body 620 may, in some embodiments, then be hung on the rail 14, with the rail in contact with the compressible cushion 626. To secure the clamping device, the user may rotate the cam member 622 from its hanging position so that the cam 640 acts on the rail and tightens the rail against the cushion 626, forcing the rail into the cushion 626 and compressing the cushion 626. As the cam 640 rotates, the projecting sidewall 646 travels along the side of the rail, preventing removal of the rail from the passage. The cam 640 is rotated until the handle 642 is disposed in the lateral passage 638.

The PIM holders disposed herein may be attached to and detached from a rail, such a rail on a patient table using only one hand, and without rotating knobs or requiring other lengthy processes. Because they may be simply attached and detached, the PIM holders may be moved during a procedure without disrupting the procedure. They may be quickly loosened and slid along the rails when desired providing convenience to a physician during a medical procedure.

It is worth noting that any of the holsters disclosed herein may be substituted and used in place of other holsters in other embodiments. Accordingly, any disclosed clamping device may be used with any disclosed holster.

Although several selected embodiments have been illustrated and described in detail, it will be understood that they are exemplary, and that a variety of substitutions and alterations are possible without departing from the spirit and scope of the present invention, as defined by the following claims.

I claim:

1. A PIM holder for attaching a PIM device having a cable to a rail in a medical environment, the PIM holder comprising:
    a holster having an open end sized to receive a PIM device and having a cable opening extending from the open end on a side adjacent the open end to a side opposite the open end; and
    a clamping device sized and configured to attach the holster to a rail, the clamping device comprising:
    a stationary jaw secured to the holster; and
    a moving jaw disposed adjacent the stationary jaw, the stationary jaw and moving jaw forming an opening that receives the rail in a lateral direction and forming a passage therebetween to capture the rail; and
    an actuator pivotable between an open position and a closed position to displace the moving jaw to open and close the clamping device,
    wherein the actuator comprises a pivot hole and a sliding slot, the pivot hole being located to correspond with a pivot hole in the stationary jaw and the sliding slot being located to correspond with a passage through the moving jaw.

2. The PIM holder of claim 1, wherein the clamping device comprises a biasing system slidably associated with the stationary jaw and connected to the moving jaw in a manner that biases the moving jaw toward the stationary jaw.

3. The PIM holder of claim 2, wherein the biasing system comprises:
    a bracket attached to the moving jaw via a fastener; and
    a biasing element biasing the bracket in a direction away from the moving jaw.

4. The PIM holder of claim 3, wherein the bracket comprises a T-shape having a body and two extending arms.

5. The PIM holder of claim 2, wherein the biasing system is structurally arranged to linearly translate the moving jaw relative to the stationary jaw.

6. The PIM holder of claim 1, wherein the stationary jaw comprises a slot configured to receive a biasing system, the biasing system comprising:
    a T-shaped bracket disposed in the slot and extending through a body of the stationary jaw; and
    biasing members adjacent the T-shaped bracket disposed within the slot and biasing the bracket away from the moving jaw in a direction out of the slot.

7. The PIM holder of claim 1, further comprising a rotation system disposed between the holster and the clamping device, the rotation system comprising:
    a first rotational element connected to the holster; and
    a second rotational element connected to the clamping device, the first rotational element being rotatable relative to the second rotational element.

8. The PIM holder of claim 7, further comprising a detent system associated with the first and second rotational elements.

9. The PIM holder of claim 1, wherein the actuator comprises a handle and a lever arms, the handle extending obliquely relative to the holster when the clamping device is in a closed position.

10. The PIM holder of claim 1, wherein the stationary jaw and the moving jaw each comprise a seat sized and shaped to receive the rail, the seat having a compressible cushion disposed therein.

11. The PIM holder of claim 1, wherein the stationary jaw and the moving jaw each comprise a seat, the seat having a first portion sized and shaped to receive a rectangular rail and shaped and having a section portion sized to receive a cylindrical rail.

* * * * *